(12) United States Patent
Tinsley et al.

(10) Patent No.: US 9,492,433 B2
(45) Date of Patent: Nov. 15, 2016

(54) PHARMACEUTICAL COMPOSITION FOR THE TREATMENT OF DUCHENNE MUSCULAR DYSTROPHY

(71) Applicant: Summit Corporation Plc, Abingdon, Oxfordshire (GB)

(72) Inventors: Jonathon Mark Tinsley, Didcot (GB); Neil Robinson, Aylesbury (GB)

(73) Assignee: Summit Corporation Plc, Abingdon, Oxfordshire (GB)

(*) Notice: Subject to any disclaimer, the term of this patent is extended or adjusted under 35 U.S.C. 154(b) by 0 days.

(21) Appl. No.: 14/537,764

(22) Filed: Nov. 10, 2014

(65) Prior Publication Data

US 2015/0238467 A1 Aug. 27, 2015

Related U.S. Application Data

(63) Continuation of application No. PCT/EP2013/059730, filed on May 10, 2013.

(30) Foreign Application Priority Data

May 10, 2012 (GB) .................... 1208178.2

(51) Int. Cl.

| | | |
|---|---|---|
| A61K 31/423 | (2006.01) | |
| A61K 9/10 | (2006.01) | |
| A61P 21/00 | (2006.01) | |
| A61K 47/10 | (2006.01) | |
| A61K 47/14 | (2006.01) | |
| A61K 9/00 | (2006.01) | |
| A61K 47/36 | (2006.01) | |
| A61K 47/38 | (2006.01) | |
| A61K 9/14 | (2006.01) | |
| A61K 47/26 | (2006.01) | |

(52) U.S. Cl.
CPC ............ *A61K 31/423* (2013.01); *A61K 9/0095* (2013.01); *A61K 9/10* (2013.01); *A61K 9/14* (2013.01); *A61K 47/10* (2013.01); *A61K 47/14* (2013.01); *A61K 47/26* (2013.01); *A61K 47/36* (2013.01); *A61K 47/38* (2013.01)

(58) Field of Classification Search
None
See application file for complete search history.

(56) References Cited

FOREIGN PATENT DOCUMENTS

| WO | WO 2007/091106 A2 | 8/2007 |
|---|---|---|
| WO | WO 2009/019504 A1 | 2/2009 |
| WO | WO 2009/021748 A2 | 2/2009 |

OTHER PUBLICATIONS

International Preliminary Report on Patentability mailed Nov. 20, 2014 for Application No. PCT/EP2013/059730.
Perkins et al., The role of utrophin in the potential therapy of Duchenne muscular dystrophy. Neuromuscul Disord. Oct. 2002;12 Suppl 1:S78-89.
Khurana et al., Pharmacological strategies for muscular dystrophy. Nat Rev Drug Discov. May 2003;2(5):379-90.
PCT/EP2013/059730, Sep. 30, 2013, International Search Report and Written Opinion.

*Primary Examiner* — H. Sarah Park
(74) *Attorney, Agent, or Firm* — Wolf, Greenfield & Sacks, P.C.

(57) ABSTRACT

This invention relates to pharmaceutical compositions comprising 5-(ethylsulfonyl)-2-(naphthalen-2-yl)benzo[d]oxazole (C1100), to processes for preparing the compositions, and to various therapeutic uses of the combinations. Also provided is a method of treatment of Duchenne muscular dystrophy or Becker muscular dystrophy using the compositions.

47 Claims, 10 Drawing Sheets

(A)

(B)  Step 1-2: Acid-catalyzed dehydration to form crude drug substance (5)

4
5-(ethylsulfonyl)-2-naphthalen-2-yl)-2-hydroxy[3H]benzo[d]oxazole
$C_{19}H_{17}NO_4S$
MW = 355.4136

5
Crude Drug Substance
5-(ethylsulfonyl)-2-(naphthalen-2-yl)benzo[d]oxazole
$C_{19}H_{15}NO_3S$
MW = 337.3982

Step 2-1: Recrystallization of crude 5 to form purified drug substance (6)

6
Purified Drug Substance
5-(ethylsulfonyl)-2-(naphthalen-2-yl)benzo[d]oxazole
$C_{19}H_{15}NO_3S$
MW = 337.3982

| |
|---|
| 1. Dispense all the required materials. |
| ↓ |
| 2. Tare a stainless steel vessel. Add around 90% of the water for injection into the vessel. |
| ↓ |
| 3. Add the Poloxamer 188 into the vessel and mix. |
| ↓ |
| 4. Add the methyl and propyl parabens into the vessel and mix. |
| ↓ |
| 5. Add the C1100 drug substance into the vessel and mix. |
| ↓ |
| 6. Pass the intermediate product through a Microfluidiser at high pressure until the required particle sizes are achieved. |
| ↓ |
| 7. Add the HPMC into the vessel and mix. |
| ↓ |
| 8. Add the glycerol into the vessel and mix. |
| ↓ |
| 9. Add the non-crystallising sorbitol into the vessel and mix. |
| ↓ |
| 10. Add the strawberry cream flavour into the vessel and mix. |
| ↓ |
| 11. Add the remaining WFI into the vessel to the final batch weight and mix. |
| ↓ |
| 12. Transfer the suspension into a bulk stainless steel vessel. Continue mixing the product overnight to fully hydrate the HPMC. |
| ↓ |
| 13. Repeat step 1 to 11 to prepare subsequent sub-lots as required. Transfer each sub-lot into the bulk vessel. Continue mixing overnight. |
| ↓ |
| 14. Fill the product into 150 mL amber glass bottles and seal bottles with a tamper evident cap (primary packaging). |
| ↓ |
| 15. Pack bottles into a cardboard box (secondary packaging) and then pack for shipment. |

PHARMACEUTICAL COMPOSITION FOR THE TREATMENT OF DUCHENNE MUSCULAR DYSTROPHY

TECHNICAL FIELD

This invention relates to pharmaceutical compositions comprising 5-(ethylsulfonyl)-2-(naphthalen-2-yl)benzo[d] oxazole (C1100), to processes for preparing the compositions, and to various therapeutic uses of the combinations. Also provided is a method of treatment of Duchenne muscular dystrophy or Becker muscular dystrophy using the compositions.

BACKGROUND OF THE INVENTION

Duchenne muscular dystrophy (DMD) is a common, genetic neuromuscular disease associated with the progressive deterioration of muscle function, first described over 150 years ago by the French neurologist, Duchenne de Boulogne, after whom the disease is named. DMD has been characterized as an X-linked recessive disorder that affects 1 in 3,500 males caused by mutations in the dystrophin gene. The gene is the largest in the human genome, encompassing 2.6 million base pairs of DNA and containing 79 exons. Approximately 60% of dystrophin mutations are large insertion or deletions that lead to frameshift errors downstream, whereas approximately 40% are point mutations or small frameshift rearrangements. The vast majority of DMD patients lack the dystrophin protein. Becker muscular dystrophy is a much milder form of DMD caused by reduction in the amount, or alteration in the size, of the dystrophin protein. The high incidence of DMD (1 in 10,000 sperm or eggs) means that genetic screening will never eliminate the disease, so an effective therapy is highly desirable.

Upregulation of utrophin, an autosomal paralogue of dystrophin has been proposed as a potential therapy for DMD (Perkins & Davies, Neuromuscul Disord, S1: S78-S89 (2002), Khurana & Davies, Nat Rev Drug Discov 2:379-390 (2003)). When utrophin is overexpressed in transgenic mdx mice it localizes to the sarcolemma of muscle cells and restores the components of the dystrophin-associated protein complex (DAPC), which prevents the dystrophic development and in turn leads to functional improvement of skeletal muscle. Adenoviral delivery of utrophin in the dog has been shown to prevent pathology. Commencement of increased utrophin expression shortly after birth in the mouse model can be effective and no toxicity is observed when utrophin is ubiquitously expressed, which is promising for the translation of this therapy to humans. Upregulation of endogenous utrophin to sufficient levels to decrease pathology might be achieved by the delivery of small diffusible compounds.

C1100 is a small molecule utrophin upregulator that has the potential to be a universal treatment for DMD.

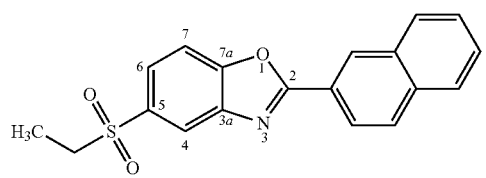

5-(ethylsulfonyl)-2-(naphthalen-2-yl)benzo[d]oxazole (C1100)

The synthesis and therapeutic use of this compound is described in our earlier WO2007/091106, while its various polymorphic forms and processes for the production of such forms are described in WO2009/021748. The compound acts in synergy with corticosteroids, including prednisone, prednisolone and deflazacort to reduce exercise-induced fatigue in mouse models of DMD (see our earlier WO2009/019504).

SUMMARY OF THE INVENTION

According to the invention there is provided a liquid pharmaceutical composition comprising an aqueous suspension of nanoparticulate C1100. The C1100 compound for use in the pharmaceutical compositions may be synthesised by any suitable methods, including those described herein and in WO2007/091106, WO2009/021748 and WO2009/019504.

In another aspect, the invention provides a process for preparing a liquid pharmaceutical composition comprising microfluidising solid C1100 in an aqueous vehicle to form a suspension of nanoparticulate C1100.

In another aspect, the invention provides a liquid pharmaceutical composition obtainable by the process of the invention.

In another aspect, the invention provides the liquid pharmaceutical composition of the invention for use in therapy or prophylaxis.

In another aspect, the invention provides the liquid pharmaceutical composition of the invention for use in the treatment or prophylaxis of Duchenne muscular dystrophy or Becker muscular dystrophy.

In another aspect, the invention provides the use of a composition of the invention for the manufacture of a medicament for use in the treatment or prophylaxis of Duchenne muscular dystrophy or Becker muscular dystrophy.

In another aspect, the invention provides a method for the treatment or prophylaxis of Duchenne muscular dystrophy or Becker muscular dystrophy in a patient in need thereof, comprising orally administering to the patient an effective amount of a composition according to the invention.

BRIEF DESCRIPTION OF THE DRAWINGS

FIG. 9 shows the process used to manufacturing the C1100 formulation.

DETAILED DESCRIPTION OF THE INVENTION

Figure 1:
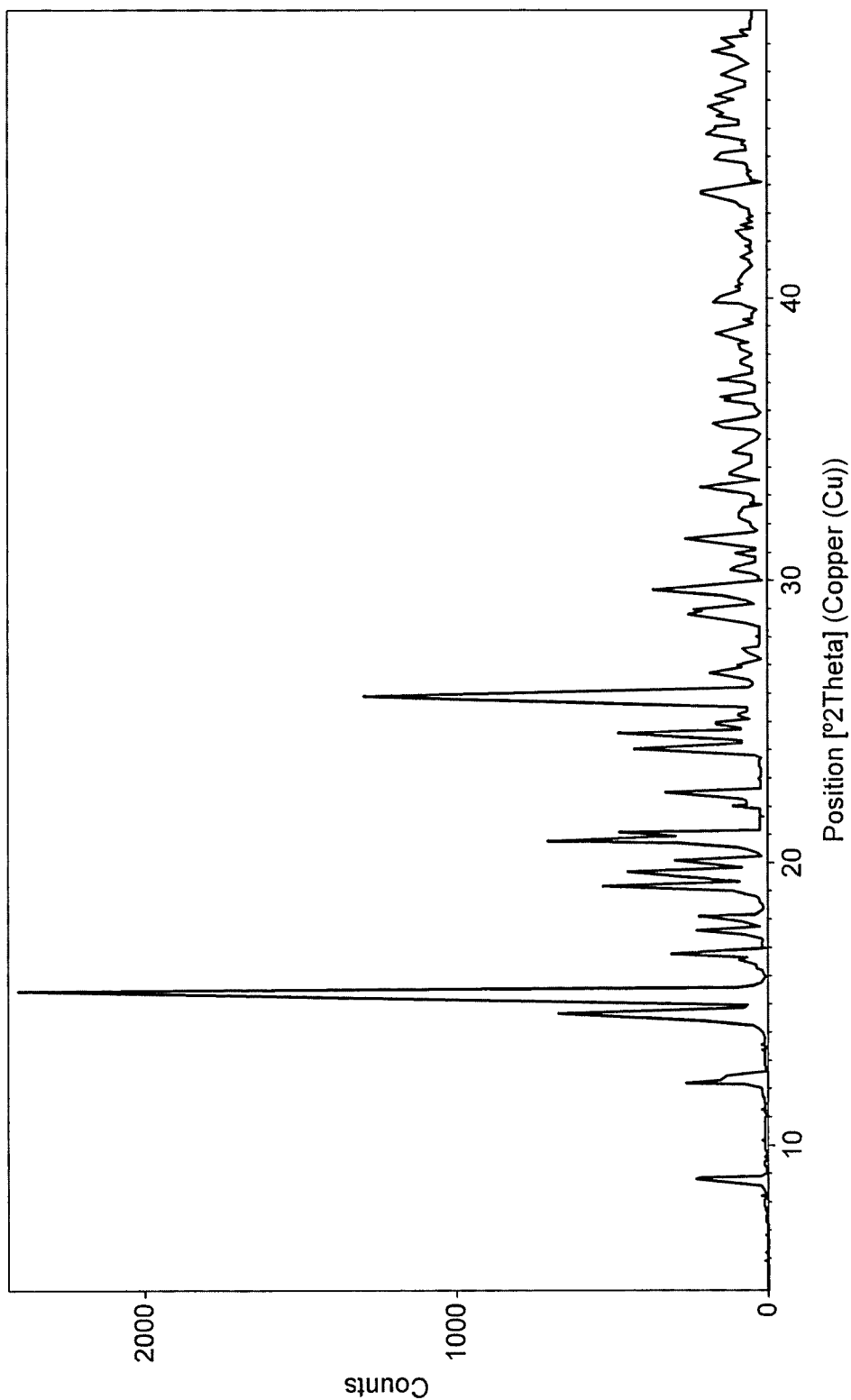
FIG. 1 shows the X-ray powder diffraction (XRPD) pattern for Form I of the drug substance.

All publications, patents, patent applications and other references mentioned herein are hereby incorporated by reference in their entireties for all purposes as if each individual publication, patent or patent application were specifically and individually indicated to be incorporated by reference and the content thereof recited in full.

DEFINITIONS AND GENERAL PREFERENCES

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The phrase "consisting essentially of" is used herein to require the specified integer(s) or steps as well as those which do not materially affect the character or function of the claimed invention.

As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

A "pharmaceutical composition" is a composition in a form, concentration and level of purity suitable for administration to a patient (e.g. a human or animal patient) upon which administration it can elicit the desired physiological changes. Pharmaceutical compositions are typically sterile and/or non-pyrogenic. The term non-pyrogenic as applied to the pharmaceutical compositions of the invention defines compositions which do not elicit undesirable inflammatory responses when administered to a patient.

As used herein, the term "nanoparticulate" as applied to a suspension or other composition herein, means particles having a $D_{50}$ particle size less than 2 μm and/or a $D_{90}$ particle size less than 7 μm.

The $D_{90}$ particle size is a parameter such that 90% by volume of particles in the composition are smaller in their longest dimension than that parameter, as measured by any conventional particle size measuring technique known to those skilled in the art. Such techniques include, for example, sedimentation field flow fractionation, photon correlation spectroscopy, light scattering (e.g. laser diffraction) and disk centrifugation.

In various embodiments of the present invention, suspensions are provided having a $D_{90}$ particle size less than: 3000 nm; 2750 nm; 2500 nm; 2250 nm; 2000 nm; 1750 nm; 1500 nm; 1250 nm or 1000 nm, for example about 1800 nm.

The $D_{50}$ particle size of a composition is a parameter such that 50% by volume of particles in the composition are smaller in their longest dimension than that parameter, as measured by any conventional particle size measuring technique known to those skilled in the art (and as described above). $D_{50}$ particle size is therefore a measure of volume median particle size but is sometimes referred to as "average" or "mean" particle size.

In various embodiments of the present invention, suspensions are provided having a $D_{90}$ particle size less than: 1500 nm; 1400 nm; 1300 nm; 1200 nm; 1100 nm; 1000 nm; 900 nm; 800 nm; 700 nm; 600 nm; 500 nm or 400 nm, for example about 600 nm.

The $D_{10}$ particle size of a composition is a parameter such that 10% by volume of particles in the composition are smaller in their longest dimension than that parameter, as measured by any conventional particle size measuring technique known to those skilled in the art (and as described above).

In various embodiments of the present invention, suspensions are provided having a $D_{10}$ particle size less than: 1000 nm; 900 nm; 800 nm; 700 nm; 600 nm; 500 nm; 400 nm; 300 nm or 200 nm, for example about 400 nm.

In various embodiments of the present invention, suspensions are provided having: a $D_{10}$ particle size less than: 1000 nm; 900 nm; 800 nm; 700 nm; 600 nm; 500 nm; 400 nm; 300 nm or 200 nm; a $D_{50}$ particle size less than: 1500 nm; 1400 nm; 1300 nm; 1200 nm; 1100 nm; 1000 nm; 900 nm; 800 nm; 700 nm; 600 nm; 500 nm or 400 nm; and a $D_{90}$ particle size less than: 3000 nm; 2750 nm; 2500 nm; 2250 nm; 2000 nm; 1750 nm; 1500 nm; 1250 nm or 1000 nm.

Preferred are suspensions having a $D_{10}$ particle size less than 400 nm, a $D_{50}$ particle size less than 600 nm and a $D_{90}$ particle size less than 1800 nm.

Also preferred are suspensions having a $D_{10}$ particle size of about 400 nm; and/or a $D_{50}$ particle size of about 600 nm; and/or a $D_{90}$ particle size of about 1800 nm.

Posology

The preferred route of administration is oral administration. The dose of the composition for therapy or prophylaxis as described herein is determined in consideration of age, body weight, general health condition, diet, administration time, administration method, clearance rate, combination of drugs, the level of disease for which the patient is under treatment then, and other factors.

The desired dose is preferably presented as a single dose for daily administration. However, two, three, four, five or six or more sub-doses administered at appropriate intervals throughout the day may also be employed.

While the dose varies depending on the target disease, condition, subject of administration, administration method and the like, for oral administration as a therapeutic agent for the treatment of Duchenne muscular dystrophy in a patient suffering from such a disease is from 0.01 mg-10 g, preferably 10-400 mg, is preferably administered in a single dose or in 2 or 3 portions per day.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1

C1100 Structure and General Properties

C1100 exhibits four polymorphic forms (Forms I-IV). The preferred form for use in the pharmaceutical compositions described herein is the thermodynamically-stable Form I polymorph, and the physical properties described in these Examples are be specific to Form I. Polymorph Form I is produced consistently by the manufacturing process described herein. It takes the form of a white to tan crystalline solid with a melting point of 160-161° C.

Solubility of C1100 Form I Polymorph

The solubility of the drug substance at 20° C. in 18 different pharmaceutically-acceptable solvents has been assessed. In each case, about 25 mg of drug substance was allowed to equilibrate with 250 µL of solvent over 4 hours. The resulting saturated solutions were filtered and analysed by HPLC. The results are given in the Table below:

| Solubility of C1100 form I polymorph | |
|---|---|
| Solvent | Solubility at 20° C. (mg/mL) |
| 1-butanol | 0.35 |
| 2-propanol | 0.47 |
| 1-propanol | 0.79 |
| 2-butanol | 0.85 |
| Methanol | 1.06 |
| Ethanol | 1.14 |
| Butan-2-one | 3.12 |
| Acetonitrile | 5.44 |
| Ethyl acetate | 8.36 |
| Toluene | 8.50 |
| Heptane | 10.93 |
| tert-butyl methyl ether (TBME) | 11.67 |
| Dimethylsulfoxide | 13.20 |
| Tetrahydrofuran | 25.92 |
| Acetone | 27.53 |
| 1,4-dioxane | 28.40 |
| Dimethylformamide | >33.81 |
| Chloroform | >50.00 |

Additionally, C1100 is practically insoluble in water (<1 µg/mL), and very slightly soluble in corn oil (0.6 mg/mL).

X-Ray Powder Diffraction

The XRPD pattern for Form I of the drug substance is shown in FIG. 1. The XRPD pattern shows a distinctive pattern of sharp peaks, demonstrating the crystalline nature of the solid.

Partition Coefficient

The water/octanol partition coefficient was determined with a ProfilerLDA isocratic chromatography system, using an octanol-coated column with octanol-saturated mobile phases. The results show that the drug substance is highly hydrophobic with log D=3.99±0.01 at pH 7.4.

Thermal Analysis

Figure 2:
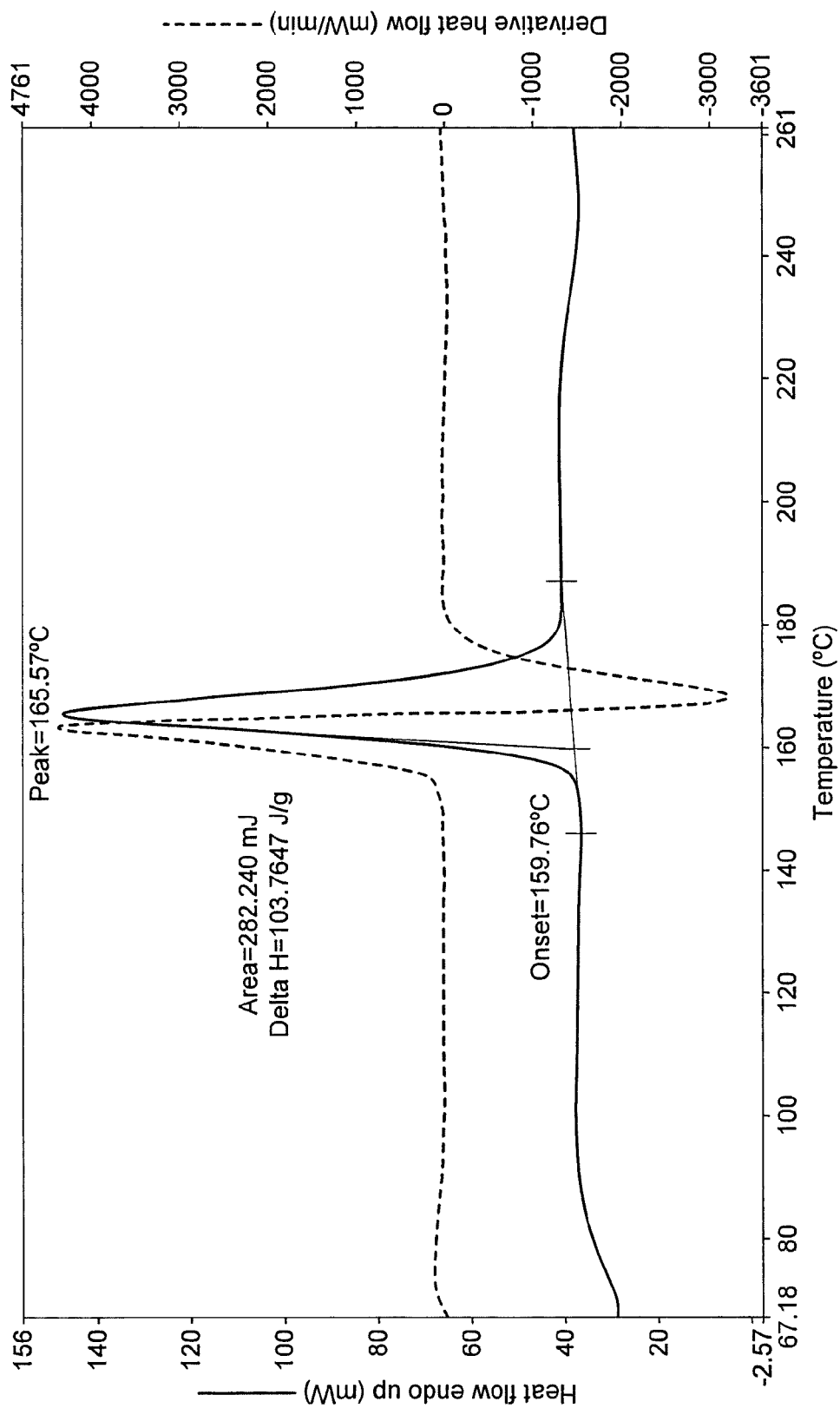
FIG. 2 shows a DSC trace.

Differential scanning calorimetry (DSC) of the drug substance was performed using a Perkin-Elmer Diamond DSC unit. DSC was performed in a range from 0° C. to 200° C. under a helium purge to prevent oxidation, with a scan rate of 200° C. per minute. The DSC trace is given in FIG. 2. The results show a single melting event, with onset of melting at 159.8° C., and a latent heat of fusion of 103.8 J/g.

Figure 3:
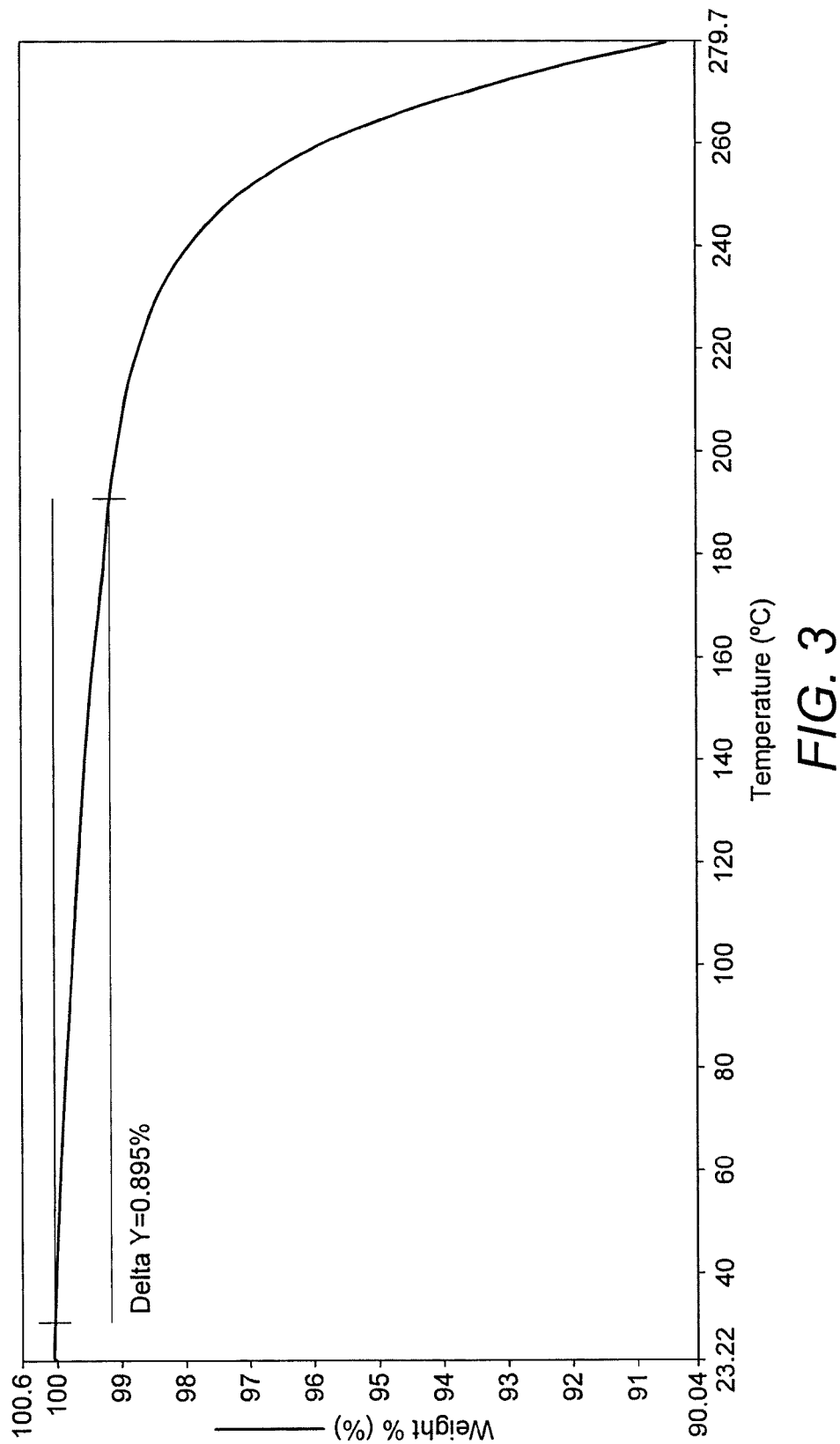
FIG. 3 shows thermal gravimetric analysis (TGA) of Form I.

Thermal gravimetric analysis (TGA) of Form I shows a loss of about 0.9% of total mass when a sample is heated from 20° C. to 250° C. at a rate of 10° C./minute (see FIG. 3). A monohydrate would be expected to lose over 5.1% of its mass through loss of water, therefore this result indicates that Form I is an anhydrous, non-solvated form. The 0.9% mass loss is most likely due to residual moisture or solvent absorbed to the surface of crystals.

Additional Characterization Data

Form I was subjected to gravimetric vapour sorption analysis, ramping profile from 0 to 90% RH at 10% RH increments. The results demonstrate that the drug substance absorbs no more than 0.25% by weight of moisture up to 90% RH, and that this slight uptake is completely reversed under dry-air conditions. Based on these results, the drug substance is not hygroscopic.

Example 2

C1100 Chemical Synthesis

Figure 4:
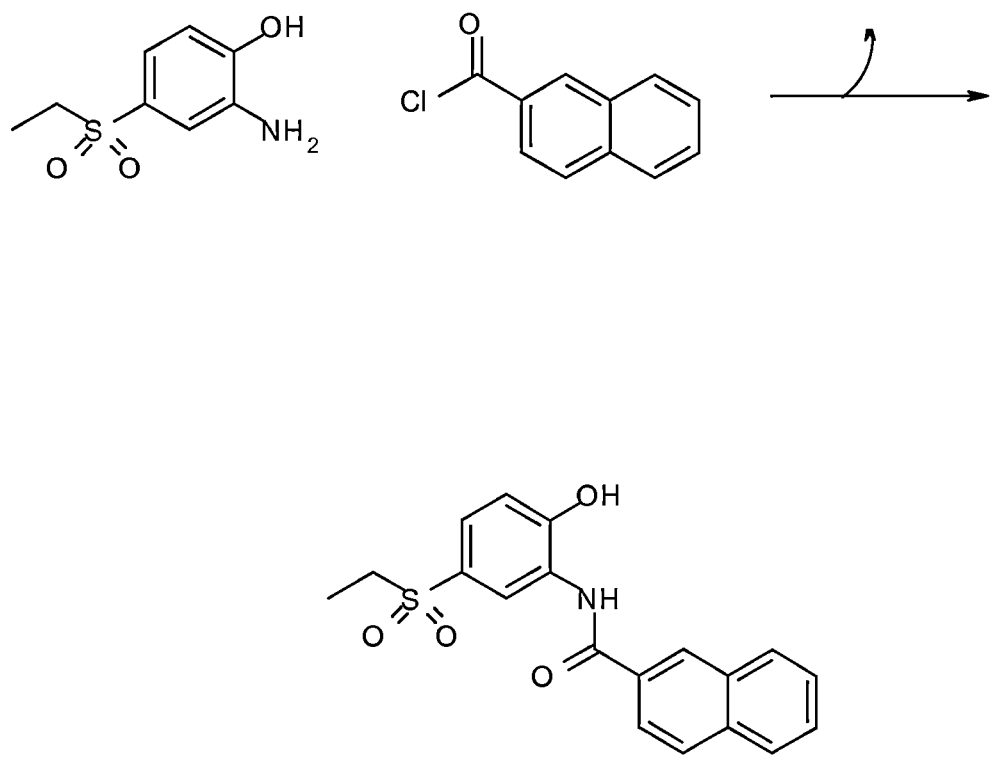
FIG. 4 shows chemical synthesis of C1100.
Figure 4:
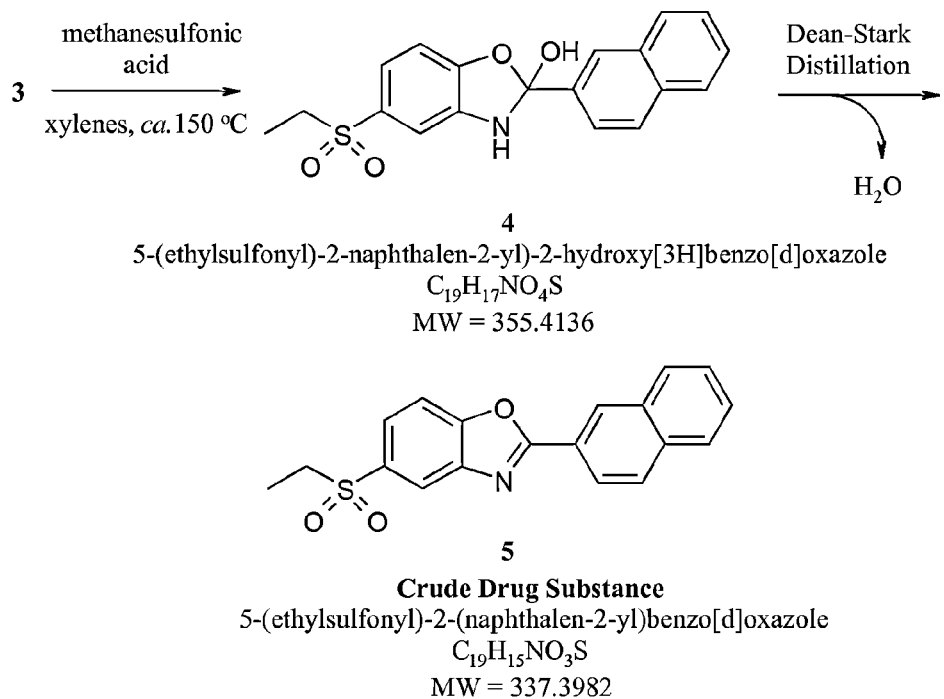
Figure 4:
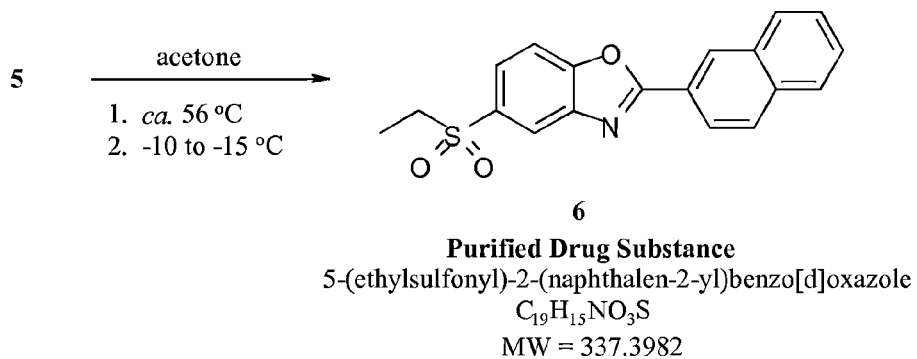

C1100 is manufactured by chemical synthesis of the crystalline product, followed by jet-milling to adjust particle size. The chemical synthesis is depicted in FIG. 4. In brief, the crude drug substance is chemically synthesised via a two-step process. The crude drug substance is then purified, and sub-lots of purified drug substance are combined and subjected to jet-milling to reduce the particle size of the material and create the final drug substance lot.

Synthesis

In step 1 (1.8 kg scale), C1100 is prepared via amide bond formation between the two GMP starting materials: 2-amino-4-(ethylsulfonyl)phenol (1) and 2-naphthoyl chloride (2) to give intermediate (3). This is followed by condensation performed in xylenes at 155° C., which leads first to cyclization (4), followed by dehydration to give a solution of the crude drug substance (5). Upon cooling, the product crystallises and is filtered and washed with tert-butyl methyl ether (TBME) prior to vacuum drying.

In step 2 (1 kg scale), crude drug substance is purified by recrystallisation from acetone. Each batch of purified drug substance is subjected to analysis to meet an intermediate specification (see Table below) prior to further processing. Purified drug substance sub-lots that meet release criteria are combined and subjected to jet-milling.

| Process | Sample | Test parameter | Specification | Test method |
|---|---|---|---|---|
| Step 1-2 (Crude drug substance) | Crude solid | Appearance | White to brown/black solid | Visual Assessment |
| | | Identity ($^1$H NMR) | Conforms with reference | USP <761> Ph. Eur. 2.2.33 |
| | | Purity (HPLC) | ≥70% (peak area) | USP <621> Ph. Eur. 2.2.46 |
| Step 2-1 (Pre-milled drug substance) | Purified crystals | Appearance | Off-white to tan solid | Visual Assessment |
| | | Identity ($^1$H NMR) | Consistent with reference | USP <761> Ph. Eur. 2.2.33 |
| | | Identity (FT-IR) | Consistent with reference | USP <197> Ph. Eur. 2.2.24 |

-continued

| Process | Sample | Test parameter | Specification | Test method |
|---------|--------|----------------|---------------|-------------|
| | | Purity (HPLC) | ≥98% (peak area) | USP <621> Ph. Eur. 2.2.46 |
| | | Residual solvents | Xylenes ≤500 ppm Acetone ≤1000 ppm TBME ≤1000 ppm | USP <467> Ph. Eur. 2.4.24 |
| | | Heavy metals (as Pb) | ≤20 ppm | USP <231> Ph. Eur. 2.4.8 |
| | | Residue on ignition (sulphated ash) | ≤1.0% | USP <281> Ph. Eur. 2.4.14 |
| | | XRPD | Form I | USP <941> Ph. Eur. 2.9.33 |

Jet-Milling

One combined purified drug substance batch is subjected to particle size reduction by jet-milling to create one bulk drug substance batch.

Control of Materials: Specifications for GMP Starting Materials

The specifications for 2-amino-4-(ethylsulfonyl)phenol (1) and 2-naphthoyl chloride (2) are provided in the Tables, below. Where necessary, purification of 1 is achieved by hot filtration in acetone, followed by recrystallisation from propan-2-ol/TBME, and 2 is purified by distillation.

Specifications for 2-amino-4-(ethylsulfonyl)phenol

| Test parameter | Specification |
|----------------|---------------|
| Appearance | Tan-brown solid |
| Identity, $^1$H NMR | Consistent with reference |
| Identity, FT-IR | Consistent with structure |
| Purity, HPLC | >98% (peak area) |
| Water content (Karl Fischer titration) | <2.0% |

Specifications for 2-naphthoyl chloride

| Test parameter | Specification |
|----------------|---------------|
| Appearance | White to yellow/green solid |
| Identity, $^1$H NMR | Consistent with structure |
| Identity, FT-IR | Consistent with reference |
| Purity, HPLC | >98% (peak area) |
| Water content (Karl Fischer titration) | <2.0% |

Reagents, Solvents and Other Materials

Argon is accepted on the supplier's certificate of analysis. Xylenes, TBME, acetone and methanesulfonic acid as reagent are passed on the suppliers certificate of analysis together with an identity test (FT-IR) and appearance against internal specifications.

Controls of Critical Steps and Intermediates

Prior to Step 2-1, recrystallisation from acetone, each batch of crude drug substance is tested to meet specified criteria. The process is also controlled at Step 2-2 (jet-milling). Before any pre-milled drug substance is combined to constitute a larger batch for jet-milling, each batch is tested to conform to in-process specifications. Any batch of purified drug substance that does not conform to standards or specifications may be reprocessed by resubmitting the batch to Step 2-1, recrystallisation from acetone. Final drug substance that has been jet-milled, but does not conform to standards or specifications, may also be reprocessed by subjecting the batch to Step 2-2.

In-process tests, limits and/or specifications are described in the Table below. Testing is performed in accordance with compendial methods (USP or Ph. Eur.).

| In-Process tests performed during synthesis of the drug substance | | | | |
|---|---|---|---|---|
| Process | Sample | Test parameter | Specification | Test method |
| Step 1-2 (Crude drug substance) | Crude solid | Appearance | White to brown/black solid | Visual Assessment |
| | | Identity ($^1$H NMR) | Conforms with reference | USP <761> Ph. Eur. 2.2.33 |
| | | Purity (HPLC) | ≥70% (peak area) | USP <621> Ph. Eur. 2.2.46 |
| Step 2-1 (Pre-milled drug substance) | Purified crystals | Appearance | Off-white to tan solid | Visual Assessment |
| | | Identity ($^1$H NMR) | Consistent with reference | USP <761> Ph. Eur. 2.2.33 |
| | | Identity (FT-IR) | Consistent with reference | USP <197> Ph. Eur. 2.2.24 |
| | | Purity (HPLC) | ≥98% (peak area) | USP <621> Ph. Eur. 2.2.46 |
| | | Residual solvents | Xylenes ≤500 ppm Acetone ≤1000 ppm TBME ≤1000 ppm | USP <467> Ph. Eur. 2.4.24 |

-continued

| In-Process tests performed during synthesis of the drug substance | | | | |
|---|---|---|---|---|
| Process | Sample | Test parameter | Specification | Test method |
| | | Heavy metals (as Pb) | ≤20 ppm | USP <231> Ph. Eur. 2.4.8 |
| | | Residue on ignition (sulphated ash) | ≤1.0 % | USP <281> Ph. Eur. 2.4.14 |
| | | XRPD | Form I | USP <941> Ph. Eur. 2.9.33 |

Process Validation and/or Evaluation

The process described above has been performed under cGMP conditions for a total of 27 batches of pre-milled drug substance and two batches of final drug substance. The synthesis and purification steps demonstrate product consistency.

Crystalline Polymorphism and X-Ray Powder Diffraction

Figure 5:
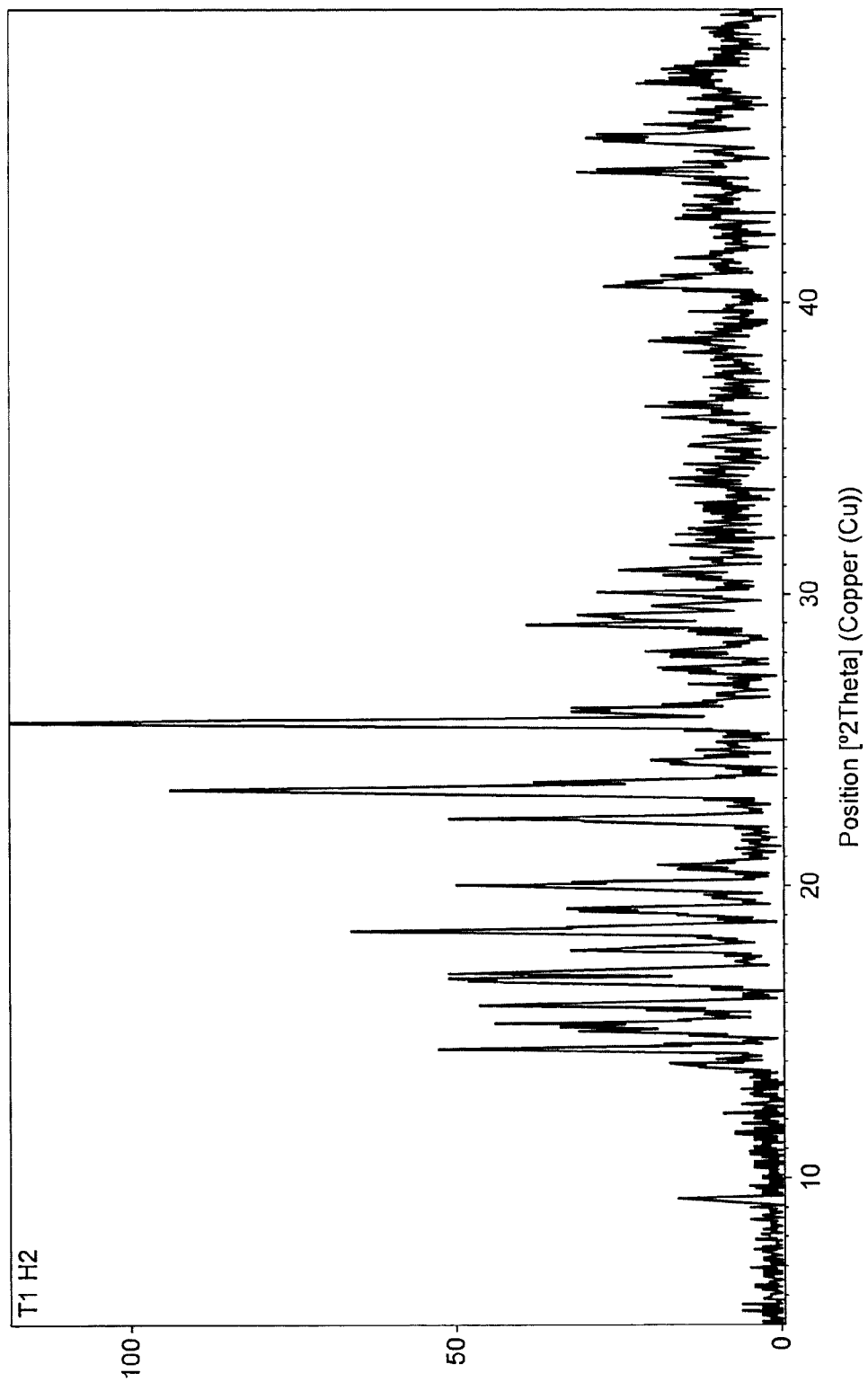
FIG. 5 shows the XRPD profile of Form II.

Two common crystalline polymorphs were identified by X-ray powder diffraction (XRPD) analysis during the development of C1100. These are identified as "Form I" and "Form II". In addition, two other rarer forms, "Form III" and "Form IV", have also been identified. Form I is the thermodynamically stable polymorph and is the form that results from recrystallisation in acetone, the procedure used in the manufacture of C1100 as described above. Form II results from recrystallisation in xylene-IPA. The XRPD profiles of polymorphs Form I and Form II are displayed in FIGS. 1 and 5, respectively.

The identity of the polymorph in the drug substance is confirmed by XRPD analysis prior to use. Some differences in relative intensities between the observed profile and the reference spectrum of FIG. 1 may be observed: such differences are common with XRPD and may be due to variations in particle size, orientation of crystals in the instrument, and different instruments.

Infrared Spectroscopy

Figure 6:
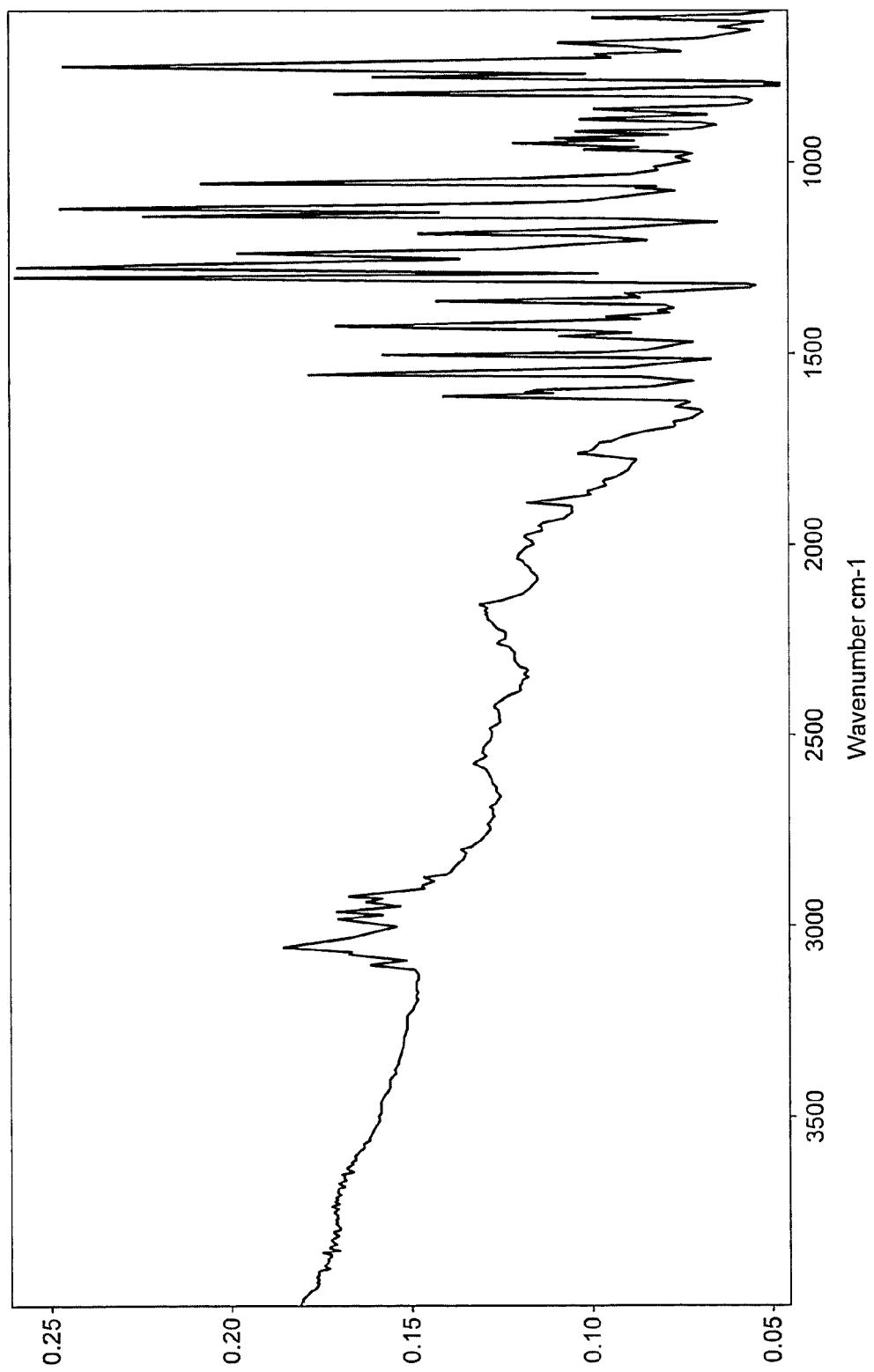
FIG. 6 shows a Fourier Transform Infrared (FT-IR) profile.

Fourier Transform Infrared (FT-IR) spectroscopy was performed using a Bruker Tensor 27 instrument fitted with a Miracle Pike ATR (Attenuated Total Reflectance) accessory. The FT-IR profile is shown in FIG. 6.

This spectrum is consistent with the expected structure of C1100. There are few peaks in the functional group region of the spectrum (wavenumbers 1500 $cm^{-1}$). The peak at 3000 $cm^{-1}$ is likely to represent the aromatic C—H stretching vibration of the naphthalene and benzoxazole moieties. There is no evidence for hydroxyl groups in this region. Peaks near 1550 and 1600 $cm^{-1}$ may represent aromatic C=C bond stretching and C=N stretching of the benzoxazole.

Raman Spectroscopy

Figure 7:
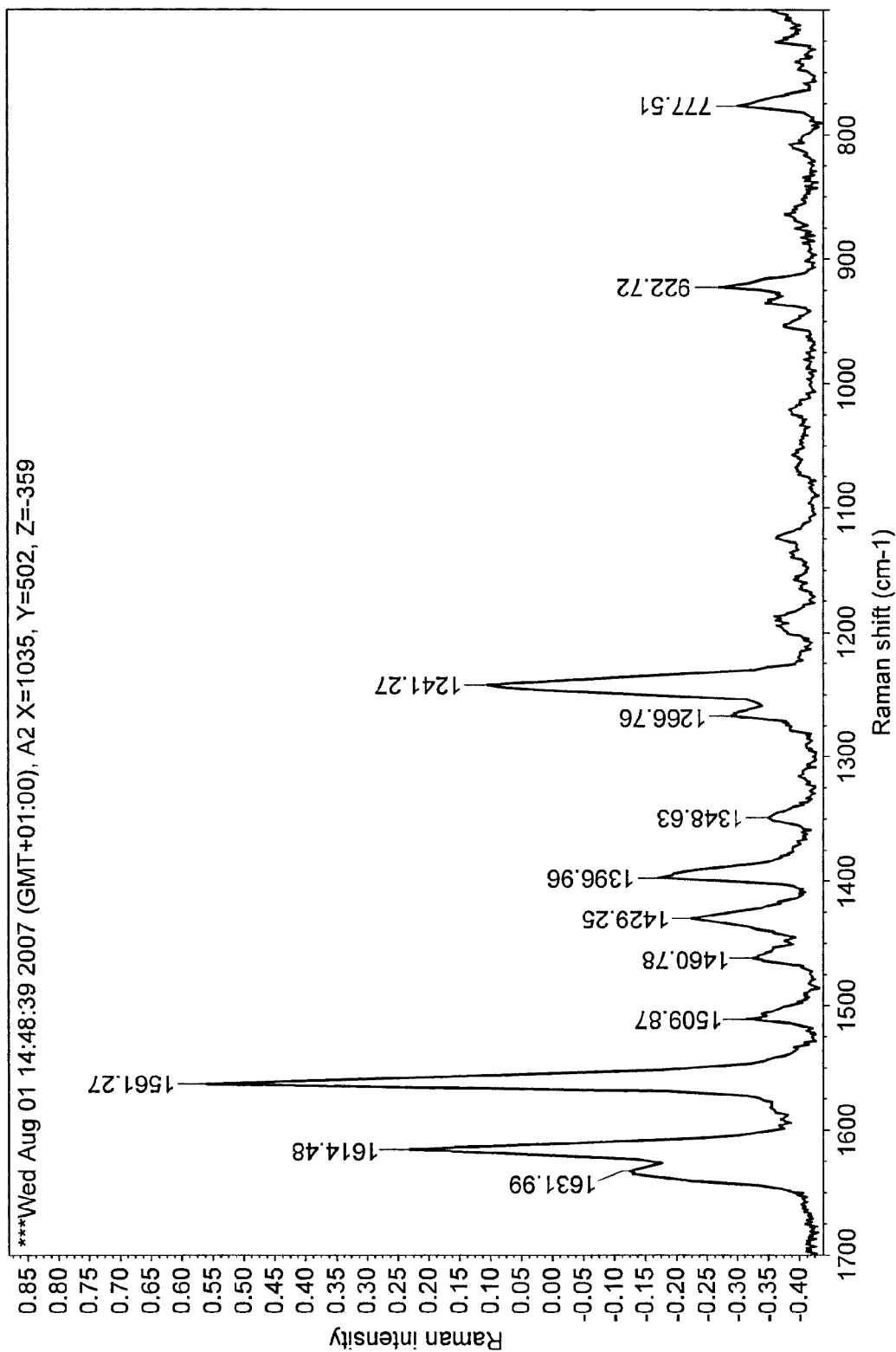
FIG. 7 shows the Raman spectrum of C1100.

The Raman spectrum of C1100 is shown in FIG. 7, and is consistent with the expected structure. The strong peaks between 1500 and 1650 $cm^{-1}$ are indicative of substituted aromatic ring structures. The peak at about 1400 $cm^{-1}$ suggests an aromatic ether (C—O—CH$_2$) stretch. Similarly, the peak near 1300 $cm^{-1}$ indicates the presence of an aromatic secondary amine.

Elemental Analysis

Elemental analysis of C1100 drug substance for C, H and N was performed using a combustion method. Sulphur content was determined using ion-coupled plasma mass spectrometry (ICP-MS). The elemental analysis results agree with expected values calculated from the molecular formula of C1100 ($C_{19}H_{15}NO_3S$), and thus provide evidence in support of the expected structure of the compound.

| Elemental analysis results for C1100 | | |
|---|---|---|
| Element | Expected value (% by mass)1 | Experimental value (% by mass) |
| C | 67.64 | 67.28 |
| H | 4.48 | 4.23 |
| N | 4.15 | 4.20 |
| O | 14.23 | 14.812 |
| S | 9.50 | 9.48 |

1Expected mass percentages were calculated from the molecular formula of C1100.
2Oxygen content was not determined experimentally. Oxygen percentages are calculated by subtraction of the values of the other elements from 100%.

Example 3

C1100 Formulation

C1100 is formulated as a white to off-white suspension for oral administration. The composition of the formulation is presented in the Table below.

| Component | Percent composition (% w/w) | Amount (g) per batch (10 kg) | Function | Reference to standard |
|---|---|---|---|---|
| C1100 | 20.000 | 2000.00 | Drug substance | In house |
| Poloxamer 188 (Lutrol F68) | 1.000 | 100.00 | Copolymer | Ph Eur |
| Methyl paraben | 0.150 | 15.00 | Preservative | Ph Eur |
| Propyl paraben | 0.015 | 1.50 | Preservative | Ph Eur |
| Hydroxypropylmethyl cellulose (Pharmacoat 645) | 1.000 | 100.00 | Copolymer | Ph Eur |
| Glycerol | 5.000 | 500.00 | Sweetener | Ph Eur |
| Non crystallizing sorbitol (70%) (Neosorb 70/70B) | 5.000 | 500.00 | Sweetener | Ph Eur |

-continued

| Component | Percent composition (% w/w) | Amount (g) per batch (10 kg) | Function | Reference to standard |
|---|---|---|---|---|
| Strawberry cream flavour (PHS-132963) | 0.800 | 80.00 | Flavour additive | Ph Eur |
| Water for injection q.s. | 100.000 | 10,000.00 | Diluent | Ph Eur |

The dose of C1100 to be administered will depend inter alia on subject body weight. The drug product can be diluted to provide the target dose concentration (preferably about 20 to 100 mg/g) using a dilution vehicle in which the proportion of each excipient in the dilution vehicle is the same as for the drug product, with additional water to compensate for the absence of drug substance.

Example 4

Manufacturing Process and Process Controls

The process used to manufacture the C1100 formulation is shown in FIG. 9,

---

1. Dispense all the required materials.
   ↓
2. Tare a stainless steel vessel. Add around 90% of the water for injection into the vessel.
   ↓
3. Add the Poloxamer 188 into the vessel and mix.
   ↓
4. Add the methyl and propyl parabens into the vessel and mix.
   ↓
5. Add the C1100 drug substance into the vessel and mix.
   ↓
6. Pass the intermediate product through a Microfluidiser at high pressure until the required particle sizes are achieved.
   ↓
7. Add the HPMC into the vessel and mix.
   ↓
8. Add the glycerol into the vessel and mix.
   ↓
9. Add the non-crystallising sorbitol into the vessel and mix.
   ↓
10. Add the strawberry cream flavour into the vessel and mix.
    ↓
11. Add the remaining WFI into the vessel to the final batch weight and mix.
    ↓
12. Transfer the suspension into a bulk stainless steel vessel. Continue mixing the product overnight to fully hydrate the HPMC.
    ↓
13. Repeat step 1 to 11 to prepare subsequent sub-lots as required. Transfer each sub-lot into the bulk vessel. Continue mixing overnight.
    ↓
14. Fill the product into 150 mL amber glass bottles and seal bottles with a tamper evident cap (primary packaging).
    ↓
15. Pack bottles into a cardboard box (secondary packaging) and then pack for shipment.

---

In brief, about 6 kg of water is added to a 15 L stainless steel vessel and a vigorous vortex and mixing pattern is created with an overhead stirrer and homogeniser. Poloxamer 188, methyl and propyl parabens and C1100 are added in sequence by spreading the powders on the surface of the water whilst mixing. The suspension mixture is then processed at high pressure through a Stansted Microfluidiser until the desired particle size is attained and collected in a suitable container. Some of the remaining water is used to wash product off of the stainless steel vessel surfaces and through the microfluidiser. The remaining excipients are added, whilst mixing, in the order shown and the remaining water is added to bring the product to the final batch weight. The suspension is then added to a 50 L stainless steel bulk container and mixed overnight to fully hydrate the HPMC.

The overhead stirrer is used to maintain the suspension and 150 mL amber glass bottles are filled with drug product (103.0 g±2.5%). Immediately after filling, each bottle is tightly sealed with a tamper-evident cap and the bottles are identification labelled, packed into cardboard boxes, and the boxes labelled. Each box contains up to six bottles.

The dilution vehicle is manufactured in a similar process, although in this process microfluidisation is not employed and 500 mL amber glass bottles are used as primary containers.

Controls of Particle Size

A critical parameter is particle size. This is assured by employing an in-process check (IPC) between Steps 6 and 7 of the flow chart above. A small (0.5 g) IPC sample is withdrawn after each pass of microfluidisation and submitted to particle size analysis. If the target particle size specification ($D_{10}$<0.4 µm; $D_{50}$<0.6 µm; $D_{90}$<1.8 µm) is not achieved, microfluidisation (Step 6) is repeated until the specification is reached.

A further IPC is made at the bottle filling stage (Step 14), in which every 25th bottle is individually tared, filled and re-weighed and the results plotted on a control chart to ensure that the fill-weight specification of 103.0 g±2.5% (i.e. 100.4 g to 105.6 g) is being met.

In the case of the dilution vehicle, an IPC is made on every 10th bottle and the specification is 506.0 g±1.0% (i.e. 500.9 g to 511.1 g).

Example 5

Analytical Procedures

Assay, Purity, and Impurities

C1100 drug product is evaluated for assay (drug substance, methyl paraben and propyl paraben) and related substances using an isocratic RP-HPLC method with an ACE C18 column (250×4.6 mm, 5 µm particle size). The mobile phase is 65% acetonitrile-35% water containing 0.1% trifluoroacetic acid; column temperature is set at 40° C. The run time is 20 minutes and detection is by ultraviolet absorbance at 210 nm. Samples are diluted in acetonitrile:water (50:50) prior to injection. Under these conditions, the C1100 elutes at a retention time of ca. 9 minutes.

Assay values are determined by comparison of sample peak area to the peak areas of a reference material. Samples are prepared with a nominal C1100 concentration of 200 µg/mL for assay of C1100; while for assay of parabens, higher concentration samples are prepared, with nominal concentrations of 30 µg/mL for methyl paraben and 3 µg/mL for propyl paraben. Overall purity, as well as the levels of individual impurities, are determined as peak area percentages (individual peak area divided by total peak area), assuming that the response factors for individual impurities are the same as that for the main peak.

The same HPLC conditions are employed for analysis of dilution vehicle, except that assay is only required for the parabens.

Identity by HPLC

Identity testing for C1100 drug product is performed using the same HPLC method outlined in the previous section. The retention time of the main peak is compared with that of the reference material main peak. The specification for identity is a relative retention time of 0.95 to 1.05 relative to that of the reference material.

In the case of dilution vehicle, identity testing is performed to confirm absence of drug substance; the specification is any peak at the retention time of drug substance reference material must have an area less than or equal to the LOQ (1 µg/mL).

Particle Size Distribution

Determination of particle size distribution is performed by laser light diffraction using a Malvern MastersizerMicroPlus particle size analyser. A solution of 1% w/v Pluronic F68 in water is used as dispersant, and a minimum of three measurements is made for each sample.

Microbial Limits

Tests for total aerobic microbial counts (TAMC), total yeasts and moulds count (TYMC), and for specific microorganisms (*E. coli*) are standard pharmacopeia methods.

Example 6

Influence of Particle Size on Pharmacokinetics

The Table below summarizes the pharmacokinetics of two formulations of C1100 after administration to the mouse. Formulation A (invention) is a nanoparticulate formulation according to the present invention in which the C1100 particles have a $D_{50}$ particle size of 0.5 µm and a $D_{90}$ particle size less than 1.1 µm. Formulation B is an otherwise similar suspension of C1100 having a larger particle size ($D_{50}$ particle size of 2.96 µm and a $D_{90}$ particle size of 7.36 µm).

| Group | $T_{max}$ (h) | $C_{max}$ (ng/mL) | $AUC_{(0\text{-}24\,h)}$ (h * ng/mL) |
| --- | --- | --- | --- |
| A (invention) | 1 | 3480 | 30700 |
| B | 0.5 | 2180 | 17700 |

It can be seen that the bioavailability of C1100 after administration of nanoparticulate formulation A is better than that achieved after administration of the micronized formulation: both the $AUC_{(0\text{-}24h)}$ and $C_{max}$ are significantly higher.

Example 7

Influence of Particle Size on Suspension Stability

Figure 8:
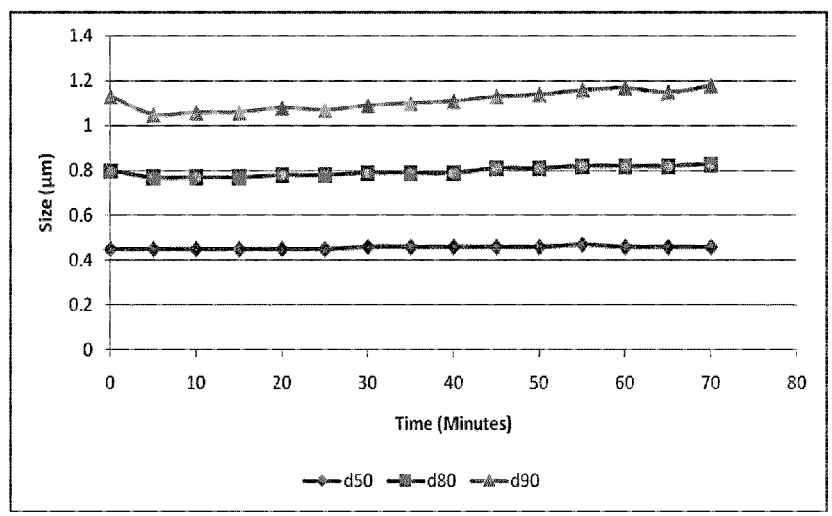
FIG. 8 shows influence of particle size on suspension stability. Part A shows Formulation A as described in Example 6 exhibits a stable particle size distribution. Part B shows the particle size of the micronized formulation increased with time.
Figure 8:
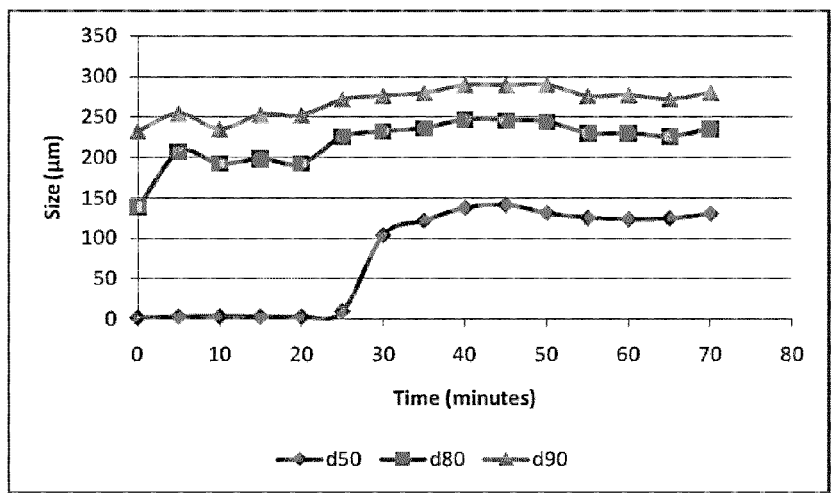

Formulation A (invention) as described in Example 6 (above) exhibits a stable particle size distribution (FIG. 8A) as compared to a micronized formulation having a larger particle size. The C1100 particles do not sediment on standing over 3 days, and no particle agglomeration (leading to an increase in particle size) was observed.

In contrast, the particle size of the micronized formulation increased with time (FIG. 8B) and the C1100 particles sedimented on standing.

Example 8

C1100 Formulation with Xanthan Burn

The composition of the formulation is presented in the Table below.

| Component | Percent composition (% w/w) | Amount (g) per batch (10 kg) | Function | Reference to standard |
| --- | --- | --- | --- | --- |
| C1100 | 20.000 | 2000.00 | Drug substance | In house |
| Poloxamer 188 (Lutrol F68) | 1.000 | 100.00 | Copolymer | Ph Eur |
| Methyl paraben | 0.150 | 15.00 | Preservative | Ph Eur |
| Propyl paraben | 0.015 | 1.50 | Preservative | Ph Eur |
| Hydroxypropylmethyl cellulose (Pharmacoat 645) | up to 1.000 | up to 100.00 | Copolymer | Ph Eur |
| Glycerol | 5.000 | 500.00 | Sweetener | Ph Eur |
| Non crystallizing sorbitol (70%) (Neosorb 70/70B) | 5.000 | 500.00 | Sweetener | Ph Eur |
| Strawberry cream flavour (PHS-132963) | 0.800 | 80.00 | Flavour additive | |
| Xanthan Gum | 0.25-1.0 | 25-50 | Stabilizer | Ph Eur |
| Water for injection q.s. | to 100.000 | — | Diluent | Ph Eur |

The pH was adjusted to 7.75 with 5 M NaOH.

This formulation exhibiting less caking than the formulation of Example 3 on storage: the suspension remained continuously dispersed on standing.

Formulations with 0.25-0.5% xanthan gum are less viscous, and may be advantageous when pour ability of the formulation is important.

The xanthan gum may replace the hydroxypropylmethyl cellulose.

A particularly preferred formulation is shown below:

| Component | Percent composition (% w/w) | Amount (g) per batch (10 kg) | Function | Reference to standard |
|---|---|---|---|---|
| C1100 | 20.000 | 2000.00 | Drug substance | In house |
| Poloxamer 188 (Lutrol F68) | 1.000 | 100.00 | Copolymer | Ph Eur |
| Methyl paraben | 0.150 | 15.00 | Preservative | Ph Eur |
| Propyl paraben | 0.015 | 1.50 | Preservative | Ph Eur |
| Hydroxypropylmethyl cellulose (Pharmacoat 645) | 1.000 | 100.00 | Copolymer | Ph Eur |
| Glycerol | 5.000 | 500.00 | Sweetener | Ph Eur |
| Non crystallizing sorbitol (70%) (Neosorb 70/70B) | 5.000 | 500.00 | Sweetener | Ph Eur |
| Strawberry cream flavour (PHS-132963) | 0.800 | 80.00 | Flavour additive | |
| Xanthan Gum | 0.25 | 25 | Stabilizer | Ph Eur |
| Water for injection q.s. | to 100.000 | — | Diluent | Ph Eur |

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A liquid pharmaceutical composition comprising an aqueous suspension of nanoparticulate 5-(ethylsulfonyl)-2-(napthalen-2-yl)benzo[d]oxazole, wherein the nanoparticles have a $D_{50}$ particle size less than 2 μm and/or a $D_{90}$ particle size less than 7 μm.

2. The composition of claim 1, wherein the nanoparticulate 5-(ethylsulfonyl)-2-(napthalen-2-yl)benzo[d]oxazole has a $D_{50}$ particle size less than 1.5 μm.

3. The composition of claim 1, wherein the nanoparticulate 5-(ethylsulfonyl)-2-(napthalen-2-yl)benzo[d]oxazole has a $D_{90}$ particle size less than 3000 nm.

4. The composition of claim 1, wherein the nanoparticulate 5-(ethylsulfonyl)-2-(napthalen-2-yl)benzo[d]oxazole has a $D_{90}$ particle size of about 1800 nm.

5. The composition of claim 1, wherein the nanoparticulate 5-(ethylsulfonyl)-2-(napthalen-2-yl)benzo[d]oxazole has: (a) a $D_{50}$ particle size less than 0.6 μm; and/or (b) a $D_{90}$ particle size less than 1.8 μm.

6. The composition of claim 1, wherein the nanoparticulate 5-(ethylsulfonyl)-2-(napthalen-2-yl)benzo[d]oxazole has the following particle size distribution (PSD): $D_{10}<1.2$ μm, $D_{50}<1.8$ μm and $D_{90}<5.4$ μm.

7. The composition of claim 1 wherein the nanoparticulate 5-(ethylsulfonyl)-2-(napthalen-2-yl)benzo[d]oxazole has the following particle size distribution (PSD): $D_{10}<0.8$ μm, $D_{50}<1.2$ μm and $D_{90}<3.6$ μm.

8. The composition of claim 1, wherein the nanoparticulate 5-(ethylsulfonyl)-2-(napthalen-2-yl)benzo[d]oxazole has the following particle size distribution (PSD): $D_{10}\leq0.4$ μm, $D_{50}: \leq0.6$ μm and $D_{90}\leq1.8$ μm.

9. The composition of claim 1, wherein the nanoparticulate 5-(ethylsulfonyl)-2-(napthalen-2-yl)benzo[d]oxazole is present as a discrete solid-state phase, wherein the solid-state phase is crystalline, semi-crystalline or amorphous form.

10. The composition of claim 9 wherein the nanoparticulate 5-(ethylsulfonyl)-2-(napthalen-2-yl)benzo[d]oxazole is present in crystalline form.

11. The composition of claim 10 wherein the crystalline form is polymorph Form I which has an X-ray diffraction pattern as shown in Figure One.

12. The composition of claim 1, wherein the 5-(ethylsulfonyl)-2-(napthalen-2-yl)benzo[d]oxazole is present in an amount of 1 to 30 wt %.

13. The composition of claim 1, wherein the 5-(ethylsulfonyl)-2-(napthalen-2-yl)benzo[d]oxazole is present in an amount of 1.5 to 20 wt %.

14. The composition of claim 1, wherein the 5-(ethylsulfonyl)-2-(napthalen-2-yl)benzo[d]oxazole is present in an amount of 2.0 to 10 wt %.

15. The composition of claim 1, further comprising at least one pharmaceutically acceptable surfactant.

16. The composition of claim 15 wherein the at least one pharmaceutically acceptable surfactant is present in an amount effective to inhibit agglomeration of the 5-(ethylsulfonyl)-2-(napthalen-2-yl)benzo[d]oxazole nanoparticles.

17. The composition of claim 15 wherein said at least one pharmaceutically acceptable surfactant is hydroxypropyl methylcellulose or a poloxamer.

18. The composition of claim 17 wherein said at least one pharmaceutically acceptable surfactant comprises hydroxypropyl methylcellulose and a poloxamer.

19. The composition of claim 15 wherein said at least one pharmaceutically acceptable surfactant is present in an amount of 0.5 to 4 wt %.

20. The composition of claim 18 wherein the hydroxypropyl methylcellulose or the poloxamer are present at 0.5 to 2 wt %.

21. The composition of claim 1 further comprising at least one preservative.

22. The composition of claim 21 wherein the preservative comprises at least one paraben.

23. The composition of claim 22 wherein said at least one paraben is methyl paraben or propyl paraben.

24. The composition of claim 23 wherein said at least one paraben comprises methyl paraben and propyl paraben.

25. The composition of claim 24 wherein the methyl paraben is present at up to 0.15 wt % and/or the propyl paraben is present at up to 0.015 wt %.

26. The composition of claim 1 further comprising at least one sweetening agent.

27. The composition of claim 26 wherein said at least one sweetening agent is glycerol or sorbitol.

28. The composition of claim 27 wherein said at least one sweetening agent comprises glycerol and sorbitol.

29. The composition of claim 28 wherein the glycerol is present at at least 5 wt % and/or the sorbitol is present at about 5 wt %.

30. The composition of claim 1 further comprising at least one flavouring agent.

31. The composition of claim 30 wherein said at least one flavouring agent comprises strawberry cream flavour.

32. The composition of claim 1 further comprising a suspension stabilizing agent.

33. The composition of claim 32 wherein the suspension stabilizing agent is xanthan gum.

34. The composition of claim 33 wherein the xantham gum is present at up to 1.0 wt %.

35. The composition of claim 1, wherein the composition has a pH of 4-8.

36. The composition of claim 1, wherein the composition is adapted for oral administration.

37. The composition of claim 1, wherein the composition consists essentially, of: (a) 2-20, 2-10 or about 20 wt % nanoparticulate 5-(ethylsulfonyl)-2-(napthalen-2-yl)benzo[d]oxazole; (b) about 0.15 wt % methyl paraben; (c) about 0.015 wt % propyl paraben; (d) about 1 wt % poloxamer 188; (e) 0-1.0, e.g. about 1 wt % hydroxypropyl methylcellulose; (f) about 0.8 wt % flavouring agent; (g) about 5 wt % glycerol; (h) about 5 wt % 70% non crystallising sorbitol; and (i) 0.25-1.0 wt % xanthan gum; the balance being (k) water.

38. A method for the treatment or prophylaxis of Duchenne muscular dystrophy or Becker muscular dystrophy in a patient in need thereof, comprising orally administering to the patient an effective amount of the composition of claim 1.

39. The composition of claim 1, wherein the nanoparticulate 5-(ethylsulfonyl)-2-(napthalen-2-yl)benzo[d]oxazole has a $D_{50}$ particle size less than 1.0 µm.

40. The composition of claim 1, wherein the nanoparticulate 5-(ethylsulfonyl)-2-(napthalen-2-yl)benzo[d]oxazole has a $D_{50}$ particle size less than 0.75 µm.

41. The composition of claim 1, wherein the nanoparticulate 5-(ethylsulfonyl)-2-(napthalen-2-yl)benzo[d]oxazole has: (a) a $D_{50}$ particle size of about 0.5 µm; and/or (b) a $D_{90}$ particle size of about 1.0 µm.

42. The composition of claim 1, wherein the nanoparticulate 5-(ethylsulfonyl)-2-(napthalen-2-yl)benzo[d]oxazole has the following particle size distribution (PSD): $D_{10}$ is ~0.4 µm, $D_{50}$ is ~0.6 µm and $D_{90}$ is ~1.8 µm.

43. The composition of claim 17, wherein said at least one pharmaceutically acceptable surfactant is poloxamer 188.

44. The composition of claim 18, wherein the poloxamer is poloxamer 188.

45. The composition of claim 25 wherein the methyl paraben is present at about 0.15 wt % and/or the propyl paraben is present at about 0.015 wt %.

46. The composition of claim 27 wherein said at least one sweetening agent is non crystallising sorbitol.

47. The composition claim 35, wherein the composition has a pH of between 7 and 8.

* * * * *